(12) United States Patent
Bhatt et al.

(10) Patent No.: US 7,490,984 B2
(45) Date of Patent: *Feb. 17, 2009

(54) METHOD OF MAKING AN IMAGING INSPECTION APPARATUS WITH IMPROVED COOLING

(75) Inventors: Ashwinkumar C. Bhatt, Endicott, NY (US); Varaprasad V. Calmidi, Binghamton, NY (US); James J. McNamara, Jr., Vestal, NY (US); Sanjeev Sathe, San Jose, CA (US)

(73) Assignee: Endicott Interconnect Technologies, Inc., Endicott, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/071,537

(22) Filed: Feb. 22, 2008

(65) Prior Publication Data

US 2008/0144768 A1 Jun. 19, 2008

Related U.S. Application Data

(62) Division of application No. 11/141,494, filed on Jun. 1, 2005, now Pat. No. 7,354,197.

(51) Int. Cl.
 *H01J 35/10* (2006.01)
 *H01J 35/12* (2006.01)
 *H05G 1/02* (2006.01)
 *G01N 23/083* (2006.01)
(52) U.S. Cl. ............................. 378/200; 378/9; 378/57
(58) Field of Classification Search ............. 378/9, 378/57, 130, 141, 199, 200
 See application file for complete search history.

(56) References Cited

U.S. PATENT DOCUMENTS

| 5,020,086 | A | 5/1991 | Peugeot |
| 5,026,983 | A | 6/1991 | Meyn |
| 5,259,012 | A | 11/1993 | Baker et al. |
| 5,367,552 | A | 11/1994 | Peschmann |
| 5,483,569 | A | 1/1996 | Annis |
| 5,524,133 | A | 6/1996 | Neale et al. |
| 5,583,904 | A | 12/1996 | Adams |
| 5,629,966 | A | 5/1997 | Dykster et al. |
| 5,991,358 | A | 11/1999 | Dolazza et al. |
| 6,018,562 | A | 1/2000 | Willson |
| 6,052,433 | A | 4/2000 | Chao |
| 6,088,423 | A * | 7/2000 | Krug et al. ............... 378/57 |
| 6,236,709 | B1 | 5/2001 | Perry et al. |
| 6,400,799 | B1 | 6/2002 | Andrews |
| 6,430,255 | B2 * | 8/2002 | Fenkart et al. ............... 378/57 |
| 6,453,003 | B1 * | 9/2002 | Springer et al. ............ 378/57 |
| 6,473,487 | B1 * | 10/2002 | Le ............................ 378/57 |
| 6,496,564 | B2 | 12/2002 | Price et al. |
| 6,529,579 | B1 | 3/2003 | Richardson |
| 6,597,760 | B2 * | 7/2003 | Beneke et al. ............. 378/57 |
| 6,619,841 | B2 | 9/2003 | Lenz |

(Continued)

*Primary Examiner*—Allen C. Ho
(74) *Attorney, Agent, or Firm*—Hinman, Howard & Katell; Mark Levy; Lawrence Fraley

(57) ABSTRACT

A method of making an imaging inspection apparatus which involves positioning a plurality of individual imaging devices (e.g., X-ray Computer Tomography scanning devices) on a frame for directing beams onto articles having objects therein to detect the objects based on established criteria. The method also involves providing a cooling structure in such a manner that it will direct cooling fluid onto the imaging devices to cool these during apparatus operation.

15 Claims, 6 Drawing Sheets

U.S. PATENT DOCUMENTS

| | | |
|---|---|---|
| 6,669,366 B2 | 12/2003 | Busse et al. |
| 6,709,156 B1 * | 3/2004 | Hell et al. .................. 378/199 |
| 6,714,626 B1 | 3/2004 | Subraya et al. |
| 6,778,635 B1 | 8/2004 | Richardson |
| 7,104,687 B2 * | 9/2006 | Okamura et al. ............ 378/200 |
| 7,233,644 B1 * | 6/2007 | Bendahan et al. ............. 378/57 |

* cited by examiner

METHOD OF MAKING AN IMAGING INSPECTION APPARATUS WITH IMPROVED COOLING

The instant application is a divisional of Ser. No. 11/141, 494, filed Jun. 1, 2005, now U.S. Pat. No. 7,354,197.

TECHNICAL FIELD

The invention relates to inspection apparatus designed for inspecting articles such as luggage, baggage, mail, etc. More particularly, the invention relates to such apparatus which utilize X-ray imaging and the like.

CROSS REFERENCE TO CO-PENDING APPLICATION

In Ser. No. 11/091,521, entitled "IMAGING INSPECTION APPARATUS", filed Mar. 29, 2005, there is defined an imaging inspection apparatus which utilizes a plurality of individual imaging inspection devices (e.g., X-ray Computer Tomography scanning devices) positioned on a frame for directing beams onto articles having objects therein to detect the objects based on established criteria. Among other features, the apparatus utilizes a conveyor which is not physically coupled to the frame having the imaging inspection devices to pass the articles along a path of travel to an inspection location within the apparatus, whereupon the inspection devices direct beams onto the article and the beams are detected and output signals provided to a processing and analysis assembly which analyzes the signals and identifies certain objects which meet the criteria. Ser. No. 11/091,521 is now U.S. Pat. No. 7,177,391.

In Ser. No. 11/141,349, entitled "IMAGING INSPECTION APPARATUS WITH DIRECTIONAL COOLING", filed concurrently herewith, there is defined an imaging inspection apparatus which utilizes a plurality of individual imaging devices (e.g., X-ray Computer Tomography scanning devices) for directing beams onto articles having objects therein to detect the objects based on established criteria. The apparatus utilizes a cooling structure for directing cooling fluid (e.g., air) toward and over the devices. Ser. No. 11/141, 349 is now U.S. Pat. No. 7,261,466.

In Ser. No. 11/141,494, entitled "IMAGING INSPECTION APPARATUS WITH IMPROVED COOLING," and filed Jun. 1, 2005, there is defined an imaging inspection apparatus which utilizes a plurality of individual imaging devices (e.g., X-ray Computer Tomography scanning devices) positioned on a frame for directing beams onto articles having objects therein to detect the objects based on established criteria. The apparatus utilizes a cooling structure to provide cooling to the imaging devices.

BACKGROUND OF THE INVENTION

Utilization of imaging inspection apparatus of the above type is known, including those which utilize X-ray imaging. Such apparatus are used to inspect articles such as personal luggage of airplane travelers at airports for such undesirable items as explosives and drugs. One particularly successful example of such apparatus is that which utilizes what is referred to in the art as "X-ray Computer Tomography" (hereinafter also referred to as, simply, XCT). XCT apparatus are in wide use in the medical field for providing medical imaging such as patient body X-rays. XCT (often referred to in the medical profession simply as "CT scanning") produces a cross sectional image from a grouping of attenuation measurements taken at different angles about an object such as a patient's chest or head, while the patient is maintained in a stationary position.

Apparatus of this type have been modified to make these adaptable to taking images for non-medical purposes. In U.S. Pat. No. 5,367,552, issued Nov. 22, 1994, for example, a rotating XCT scanning unit is used which requires an object to remain stationary during scanning. This apparatus is designed for detecting concealed objects, such as explosives, drugs, or other contraband in a person's luggage. The apparatus uses scanning to identify concealed objects with a density corresponding to the density of target objects such as explosives or drugs. To reduce the amount of scanning required, a number of pre-scanning approaches are described in this patent. Based upon pre-scan data, selected locations for scanning are identified. The resulting scan data is utilized to automatically identify objects of interest, which identification is further verified through automatic analysis of such attributes as shape, texture, context, and X-ray diffraction. The objects of interest are then reconstructed and displayed on a computer monitor for visual analysis by the apparatus operator.

To successfully accomplish high speed scanning, such as that useful for scanning luggage of large numbers of travelers in a relatively shorter time period than provided by conventional stationary apparatus, even further modifications have been made. One such apparatus is described in U.S. Pat. No. 6,236,709, issued May 22, 2001, in which a continuous, XCT imaging system includes a conveyor which moves a closed package for being scanned along the conveyor past three spaced sensing stations. At each sensing station a plurality of X-ray sources each emit a fan beam in the same scan plane which passes through the package to a plurality of detectors opposite the X-ray sources. One scan is a vertical perpendicular scan plane relative to the direction of travel of the package along the conveyor belt and the remaining two scan planes are horizontal scan planes at right angles and transverse to the direction of travel. One horizontal scan plane is a left to right scan plane while the remaining scan plane is a right to left scan plane. Each detector provides multiple energy outputs for the same data point in a scan slice, and the detector outputs are stored until all three sensing stations have scanned the same cross sectional view of the package in three directions. Scans are sequentially taken as the package moves continuously through the sensing stations and scanned data corresponding to cross sectional views of the package is accumulated. The stored data is calibrated and normalized and then used in a Computer Tomographic algebraic reconstruction technique. This is described in this patent as a "multi-spectral CT reconstruction", where the density of a reconstructed object is determined by the attenuation which it causes in the scanning X-rays while the atomic number of the object is determined from the multiple energy scan output. In a classifier, the density and atomic number are compared to a table containing density and atomic number identification values for specific objects to be located.

Additional examples of various scanning apparatus systems are shown and described in the following U.S. Patents.

U.S. Pat. No. 6,052,433, issued Apr. 18, 2000, describes an apparatus for performing dual-energy X-ray imaging using two-dimensional detectors. The apparatus consists of an X-ray source, a 2-dimensional X-ray detector, a beam selector, and a second 2-dimensional X-ray detector. The subject is located between the X-ray source and first detector. The beam selector prevents primary X-rays from reaching selected locations of the second (rear) detector. A pair of primary dual-energy images is obtained at the rear detector. Using a dual-energy data decomposition method, a low-resolution primary X-ray first detector image is calculated, from which a high-resolution primary dual-energy image pair is calculated. In addition, the data decomposition method is used to calculate a pair of high-spatial-resolution material composition images.

U.S. Pat. No. 6,018,562, issued Jan. 25, 2000, describes an apparatus for automatic recognition and identification of concealed objects and features thereof, such as contraband in baggage or defects in articles of manufacture. The apparatus uses multiple energy X-ray scanning to identify targets having a spectral response corresponding to a known response of targets of interest. Detection sensitivity for both automatic detection and manual inspection are improved through the multiple-energy, multi-spectral technique. Multi-channel processing is used to achieve high throughput capability. Target identification may be verified through further analysis of such attributes as shape, texture, and context of the scan data. The apparatus uses a statistical analysis to predict the confidence level of a particular target identification. A radiograph, CT image, or both may be reconstructed and displayed on a computer monitor for visual analysis by the apparatus operator. Finally, the apparatus may receive and store input from the operator for use in subsequent target identification.

U.S. Pat. No. 5,991,358, issued Nov. 23, 1999, describes a data acquisition system for use in a CT scanner which consists of an analog-to-digital converter for generating digital signals in response to analog signals representative of projection data taken at a relatively constant sampling rate. The apparatus also uses an interpolation filter for generating projection data for a plurality of predetermined projection angles as a function of the digital signals irrespective of the sampling rate. This patent references a known system which includes an array of individual detectors disposed as a single row in the shape of an arc of a circle having a center of curvature at a certain point, referred to as the "focal spot", where the radiation emanates from the X-ray source. The X-ray source and the array of detectors in this known system are positioned so that the X-ray paths between the source and each of the detectors all lie in the same plane (hereinafter the "rotation plane" or "scanning plane") which is normal to the rotation axis of the disk. Since the X-ray paths originate from what is substantially a point source and extend at different angles to the detectors, the X-ray paths form a "fan beam." The X-rays incident on a single detector at a measuring interval during a scan are commonly referred to as a "ray", and each detector generates an analog output signal indicative of the intensity of its corresponding ray. Since each ray is partially attenuated by all the mass in its path, the analog output signal generated by each detector is representative of an integral of the density of all the mass disposed between that detector and the X-ray source (i.e., the density of the mass lying in the detector's corresponding ray path) for that measuring interval.

U.S. Pat. No. 5,629,966, issued May 13, 1997, describes a real time radiographic test system which consists of a protective housing and a conveyor for conveying articles to be tested through the housing. A real time radiographic test instrument is located in the housing for performing a real time radiographic test on the article. The test instrument includes X-ray equipment disposed for directing an X-ray beam within the housing in a direction which does not intersect the conveyor. An article-handling actuator is located in the housing for repositioning an article from the conveyor to a position in registry with the X-ray beam, for maintaining the article in registry with the X-ray beam while the real time radiographic test is performed on the article and thereafter returning the article to the conveyor. The article-handling actuator and the X-ray equipment are designed such that each article to be tested is positioned substantially identically relative to the X-ray beam.

U.S. Pat. No. 5,583,904, issued Dec. 10, 1996, describes a laminography system that allows generation of high speed and high resolution X-ray laminographs by using a continuous scan method with two or more linear detectors and one or more collimated X-ray sources. Discrete X-ray images, with different viewing angles, are generated by each detector. The discrete X-ray images are then combined by a computer to generate laminographic images of different planes in the object under test, or analyzed in such a manner to derive useful data about the object under test. This system does not require any motion of the source or detectors, but simply a coordinated linear motion of the object under test. Higher speed is achieved over conventional laminography systems due to the continuous nature of the scan, and due to the ability to generate any plane of data in the object under test without having to re-image the object.

U.S. Pat. No. 5,524,133, issued Jun. 24, 1996, describes an X-ray analysis device for determining the mean atomic number of a material mass by locating a broad band X-ray source on one side of a testing station and on the other, a detector, comprising a target having X-ray detectors positioned adjacent thereto. One of the detectors is positioned and adapted to receive X-rays scattered by the detector target in a generally rearward direction and the other detector is positioned and adapted to detect forwardly propagating X-rays scattered off axis typically by more than 30 degrees, due to so-called "Compton scatter." Each of the X-ray detectors provides signals proportional to the number of X-ray photons incident thereon. The apparatus further includes means responsive to the two detector outputs which form a ratio of the number of photons detected by the two detectors and forms a numerical value thereof. A look-up table containing mean atomic numbers for given numerical ratios for different materials is used, as is a means for determining from the look-up table the atomic number corresponding to the numerical ratio obtained from the outputs of the two detectors. The atomic number is provided as an output signal.

U.S. Pat. No. 5,483,569, issued Jan. 9, 1996, describes an inspection system for inspecting objects with "penetrating radiation" having a conveyor with first and second portions which are separated by a gap. Illumination by this radiation is provided in a scanning plane which is located in the gap, and the system may be used for the inspection of thin objects. Additionally, the illumination may be arranged in the inspection of normal size objects, e.g., suitcases or cargo boxes, so that it does not include a ray which is perpendicular to any face of the object. Further, the relative orientation of the scanning plane and the faces of the object may be arranged so that the illumination does not include a ray which is parallel to any face of the object. A scanning configuration wherein the illumination does not include a ray which is perpendicular or parallel to any face of an object having parallel faces, for example, a rectangular solid, results in a display projection of the object which appears to be three dimensional.

U.S. Pat. No. 5,259,012, issued Nov. 2, 1993, describes a system which enables multiple locations within an object to be imaged without mechanical movement of the object. The object is interposed between a rotating X-ray source and a synchronized rotating detector. A focal plane within the object is imaged onto the detector so that a cross-sectional image of the object is produced. The X-ray source is produced by deflecting an electron beam onto a target anode. The target anode emits X-ray radiation where the electrons are incident upon the target. The electron beam is produced by an electron gun which includes X and Y deflection coils for deflecting the electron beam in the X and Y directions. Deflection voltage signals are applied to the X and Y deflection coils, and cause the X-ray source to rotate in a circular trace path. An additional DC voltage applied to the X or Y deflection coil will cause the circular path traced by the X-ray source to shift in the X or Y direction by a distance proportional to the magnitude of the DC voltage. This causes a different field of view, which is displaced in the X or Y direction from the previously imaged region, to be imaged. Changes in the radius of the X-ray source path result in a change in the Z level of the imaged focal plane.

U.S. Pat. No. 5,026,983, issued Jun. 25, 1991, describes an apparatus for examining food products for undesired ingredients by means of laser irradiation. A laser beam scans the food products according to a predetermined pattern. Variations in the intensity of the laser beam passing through the food products indicate the presence of undesired ingredients. This method is carried out by an apparatus which comprises two parabolic mirrors, a laser emitting a laser beam so as to originate from the focus of one of the mirrors and a detection means positioned in the focus of the other mirror. The food products are moved between the mirrors by conveyor belts.

U.S. Pat. No. 5,020,086, issued May 28, 1991, describes a situation where an object is scanned by an X-ray beam from a circular position on a target resulting from the electron beam being scanned in a circle by appropriate control signals from a beam controller and applied to the deflection coils of a microfocus X-ray tube. Tomosynthesis is accomplished by the well-known method of in-register combination of a series of digital X-ray images produced by X-ray beams emanating from different locations. This is achieved by positioning an X-ray source at multiple points on a circle around a central axis. This system eliminates some mechanical motion in that the detector does not have to rotate. However, practical limitations of pixel size and resolution tend to limit this system to inspection of items with small fields of view. Additionally, the system still requires an X, Y table to position the object under the field of view.

The above patents, and those listed below, are incorporated herein by reference.

The accurate, rapid inspection of moving articles such as multiple luggage pieces, often having many different sizes and shapes, is, understandably, a relatively difficult task, as indicated by just some of the difficulties mentioned in some of the above patents and elsewhere in the literature pertaining to this art with respect to articles in both stationary and moving positions. When utilizing many heat-generating devices such as X-ray sources, it is essential that these sources operate at the proper temperature. Otherwise, the devices may be subject to failure, which is costly in both replacement terms as well as apparatus shutdown. Maintaining these heat-generating devices at proper temperature is thus critical to assuring effective apparatus operation.

The following patents describe various means for cooling heat sources such as X-ray sources.

In U.S. Pat. No. 6,400,799, issued Jun. 4, 2002, there is described an x-ray tube cooling system which utilizes a shield structure connected between a cathode cylinder and an x-ray tube housing and disposed between the electron source and the target anode. The system uses a plurality of cooling fins to improve overall cooling of the x-ray tube and the shield so as to extend the life of the x-ray tube and related components. When immersed in a reservoir of coolant fluid, the fins facilitate improved heat transfer by convection from the shield to the to the coolant fluid. The cooling effect achieved with the cooling fins is further augmented by a convective cooling system provided by a plurality of passageways formed within the shield, which are used to provide a fluid path to the coolant. In particular, a cooling unit takes fluid from the reservoir, cools the fluid, and then circulates the cooled fluid through cooling passages. The coolant is then output from the passageway and directed over the cooling fins. In some embodiments, the passageways are oriented so as to provide a greater heat transfer rate in certain sections of the shield than in other sections.

In U.S. Pat. No. 6,496,564, issued Dec. 17, 2002, there is described an X-ray system with an X-ray "generating device" which includes an X-ray tube mounted in a casing holding a circulating, cooling medium. According to the description, the X-ray generating device includes a support mechanism mounted within the X-ray generating device in a manner for adjustably positioning, relative to the casing, the focal spot alignment path of generated X-rays. Additionally, the device includes a cooling mechanism having an inlet chamber for channeling the cooling medium within the support mechanism. Still further, a cooling stem may be positioned within the inlet chamber to increase the heat exchange surface area exposed to the cooling medium.

In U.S. Pat. No. 6,529,579, issued Mar. 4, 2003, there is described a cooling system for high-powered X-ray tubes. The cooling system includes a reservoir containing liquid coolant, in which the high-powered X-ray tube is partially immersed. In general, the liquid coolant is cooled and then circulated through the reservoir by an external cooling unit. The cooling system also includes a shield structure attached to the vacuum enclosure of the X-ray tube and disposed substantially about the aperture portion of the vacuum enclosure, thereby defining a flow passage proximate the aperture portion. Liquid coolant supplied by the external cooling unit enters the flow passage by way of an inlet port in the shield structure. After passing through the flow passage and transferring heat out of the aperture portion, the liquid coolant is discharged through an outlet port in the shield structure and enters the reservoir to repeat the cycle.

In U.S. Pat. No. 6,619,841, issued Sep. 16, 2003, there is described a fluid-cooled X-ray tube which includes a closed coolant "circuit" in which coolant circulates for the elimination of generated heat. In order to improve the cooling capacity, micro-capsules containing a phase-change material (PCM) are added to the coolant. In this arrangement, heat arising from the X-ray tube is intermediately stored in the PCM storage elements for a certain time span. Dependent on the selected material of the PCM and the amount of the PCM storage elements introduced into the coolant, the temperature of the coolant can be kept nearly constant over a specific time segment despite the heat arising from the tube during X-ray generation. Compared to conventional measures for cooling an X-ray tube, this patent mentions that the rise in temperature of the coolant is retarded by this arrangement, so that the X-ray radiator can be more highly stressed (loaded) over the same operating duration, or the operating duration of the X-radiator can be significantly lengthened given the same load. Described PCM materials for this purpose are parafins whose melting temperatures lie between 90 and 112 degrees Celsius. Mentioned alternatives to paraffin include fatty alcohols, fatty acids, hydrates of sodium carbonate, sodium acetate, calcium chloride and lithium magnesium nitrate.

In U.S. Pat. No. 6,669,366, issued Dec. 30, 2003, there is described an X-ray examination apparatus in which the X-ray detector and the X-ray source are subject to keeping the temperature constant and to cooling by way of a common cooling "circuit". A cooling medium of constant temperature is applied to the X-ray detector in order to make the detector operate at desired temperatures. The temperature of the cooling medium, increased a first time, allegedly performs cooling of the X-ray source. The heated cooling medium, after application to the X-ray detector, is applied to the X-ray source where a second exchange of heat takes place, so the X-ray source is cooled without utilizing an additional cooling circuit.

In U.S. Pat. No. 6,709,156, issued Mar. 23, 2004, there is described a cooling device for an X-ray source that is arranged in a gantry around a rotational axis. The device includes a ring-like heat exchanger that is oriented at the gantry and is thermally connected to the X-ray source. The cooling device is useable in a computed tomography apparatus having the X-ray source.

In U.S. Pat. No. 6,714,626, issued Mar. 30, 2004, there is described an x-ray tube cooling assembly which includes an electron collector body coupled to an x-ray tube window and having a first coolant circuit. The coolant circuit includes a coolant inlet and a coolant outlet. The coolant outlet directs coolant at an x-ray tube window surface to impinge upon and cool the x-ray tube window. The coolant is reflected off the reflection surface to impinge upon and cool the x-ray tube window.

In U.S. Pat. No. 6,778,635, issued Aug. 17, 2004, there is described an x-ray tube cooling system which utilizes a heat sink partially disposed within an evacuated housing of the x-ray tube and having a cooling block partially received within the bearing housing to absorb heat transmitted to the bearing assembly and bearing housing. Extended surfaces are disposed in a coolant chamber defined by the cooling block and a shell within which the cooling block is partially received. The shell defines a coolant chamber entrance and coolant chamber exit in fluid communication with the coolant chamber. The coolant chamber entrance and exit communicate with corresponding coolant inlet and outlet passageways, respectively, cooperatively defined by a pair of insulators which retain the heat sink in a predetermined orientation within an evacuated envelope of an x-ray device. A circulating coolant contacts the extended surfaces and thereby removes heat from various structures of the x-ray device.

The present invention defines a new and unique method of making an inspection apparatus which, in one embodiment, uses imaging technology (e.g., XCT scanning), in such a manner that effective cooling of the scanning devices is assured. Such cooling is accomplished for a number of scanning devices in a new and unique manner representing a significant improvement over cooling apparatus such as described above. It is believed that such an inspection apparatus would constitute a significant advancement in the art.

OBJECTS AND SUMMARY OF THE INVENTION

It is a primary object of the present invention to enhance the imaging inspection apparatus art.

It is another object of the invention to provide a method of making an imaging inspection apparatus which may be accomplished in a facile manner.

According to one aspect of the invention, there is provided a method of making an imaging inspection apparatus for inspecting objects located within articles, this method comprising providing a frame structure including a plurality of passages therein and an inspection location located substantially therein, positioning from twenty to forty XCT scanning devices on the frame structure adjacent the inspection location, these XCT scanning devices adapted for directing X-rays onto articles at the inspection location to thereby inspect the articles and for providing output signals as a result of this inspecting, positioning a processing and analysis assembly on the frame structure, this processing and analysis assembly adapted for receiving the output signals from the XCT scanning devices and analyzing these signals to identify the objects within the articles, and providing a cooling structure for directing cooling fluid through the plurality of passages within the frame structure relative to the XCT scanning devices to cool the XCT scanning devices during operation thereof.

BEST MODE FOR CARRYING OUT THE INVENTION

For a better understanding of the present invention, together with other and further objects, advantages and capabilities thereof, reference is made to the following disclosure and appended claims in connection with the above-described drawings. Like figure numbers will be used from FIG. to FIG. to identify like elements in these drawings.

Figure 1:
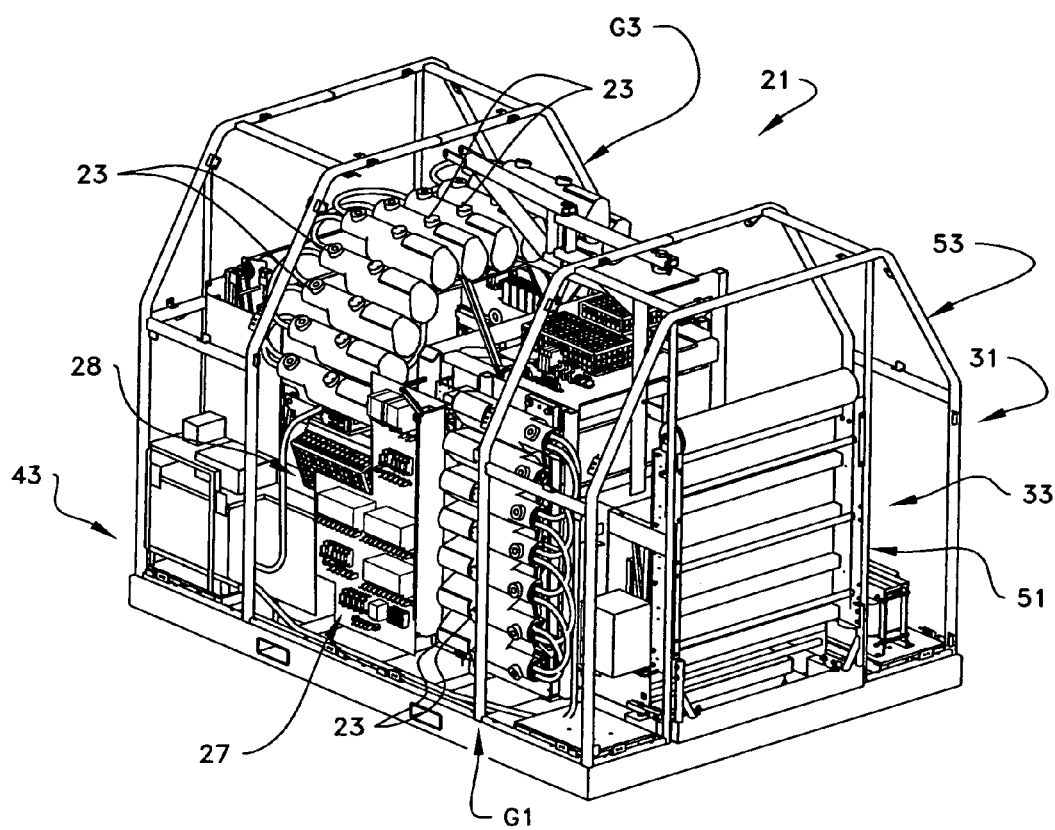
FIG. 1 is a front perspective view of an imaging inspection apparatus for inspecting objects located within articles, made using the teachings of one embodiment of the invention.
Figure 2:
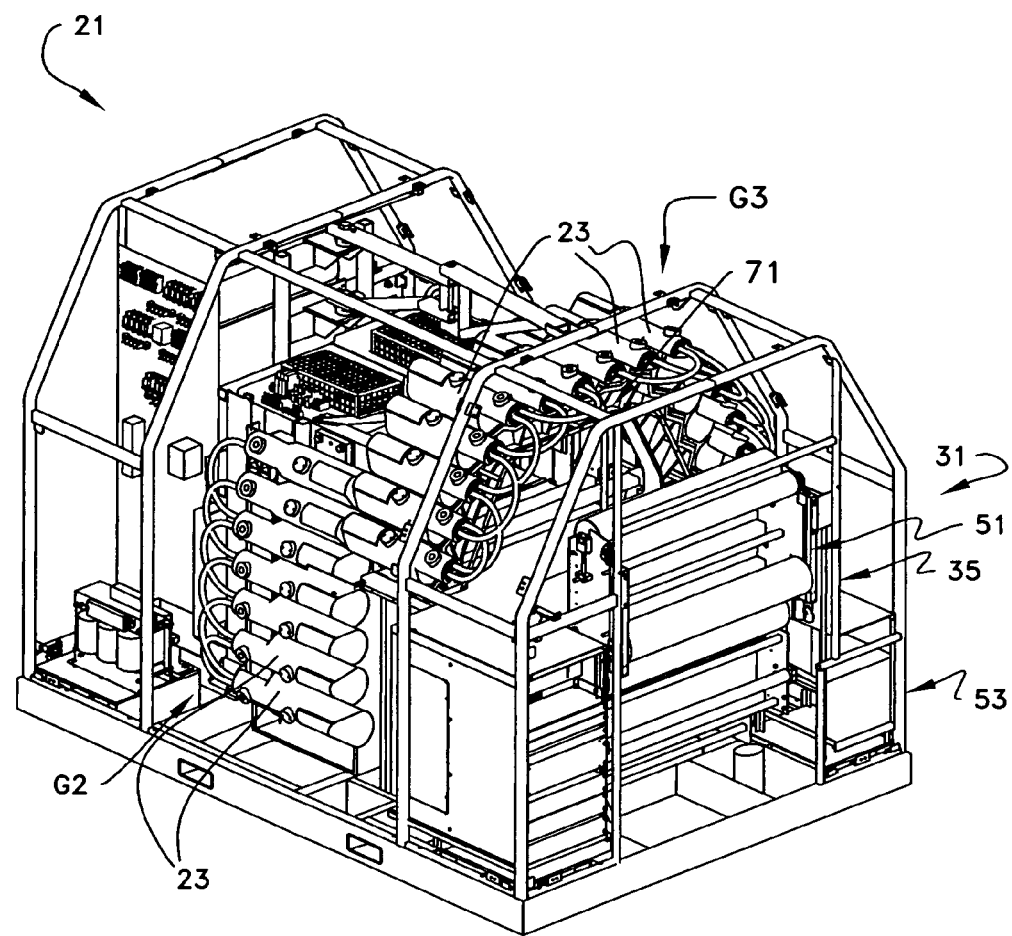
FIG. 2 is a rear perspective view of the imaging inspection apparatus for inspecting objects located within articles as shown in FIG. 1.
Figure 5:
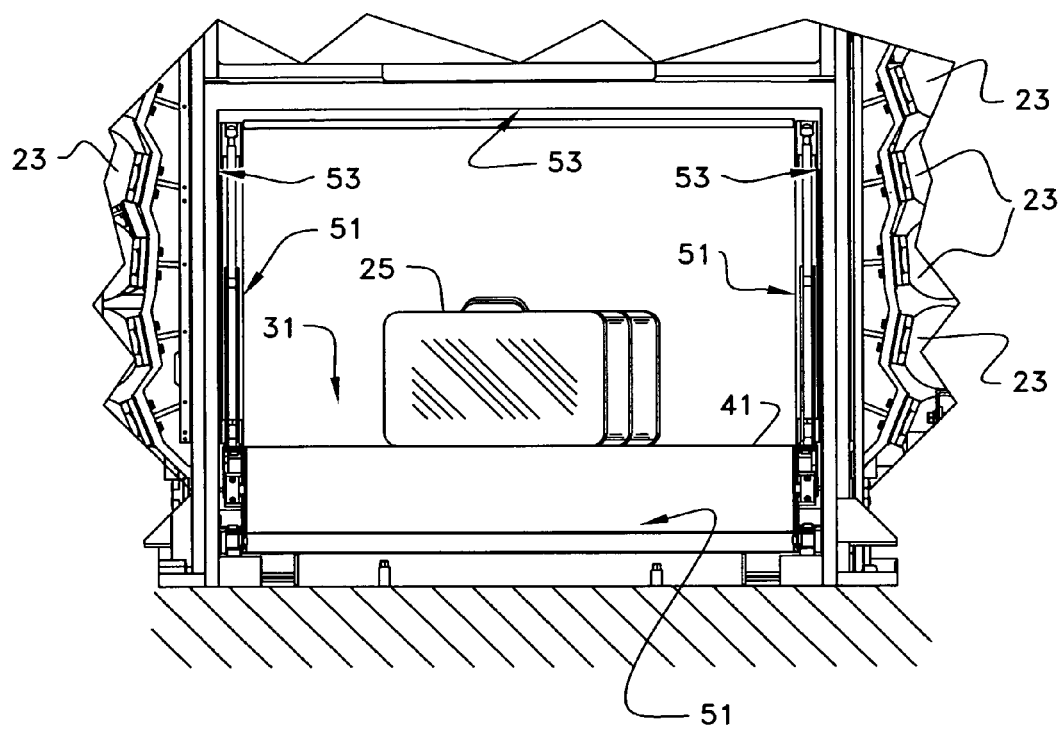
FIG. 5 is a partial end view of the apparatus of FIGS. 1 and 2, on an enlarged scale over the views of FIGS. 1-4.

In FIGS. 1 and 2, there is illustrated an imaging inspection apparatus 21 which is made according to one embodiment of the method taught herein as defined below. As indicated, apparatus 21 is particularly designed for inspecting (and detecting) objects (not shown) which might be located within closed articles such as personal luggage of an airplane traveler. As such, the apparatus is ideally designed for placement and use within an airport or other transportation facility in which large numbers of such articles are received and transported. Apparatus 21 is adapted for inspecting and detecting concealed objects such as explosives, weapons, etc., including in solid and powder form. Further explanation of how apparatus operates is provided below. One example of such an article, this being a suitcase (luggage) 25, is shown in FIG. 5. Understandably, the apparatus inspects several such articles as these articles move there-through, should the apparatus utilize a conveyor, as is preferred. The invention is not limited to apparatus using conveyors, however, as the teachings herein apply to any apparatus of this type in which heat-generating Apparatus 21 includes a plurality of imaging inspection devices 23, which, in a preferred embodiment, are individual X-ray Computer Tomography (XCT scanning devices. That is, each device is preferably an individual X-ray photon source, which is collimated to provide what may be referred to as a "fan beam." In one embodiment, these fan beams will each be collimated to a beam thickness of about 1 mm. over a distance of at least about 141 cm, with a divergence of about 0.7 milli-radians (or about 0.04 degree). Beams of such dimensions are preferred to substantially prevent background scatter and radiation leakage.

Figure 6:
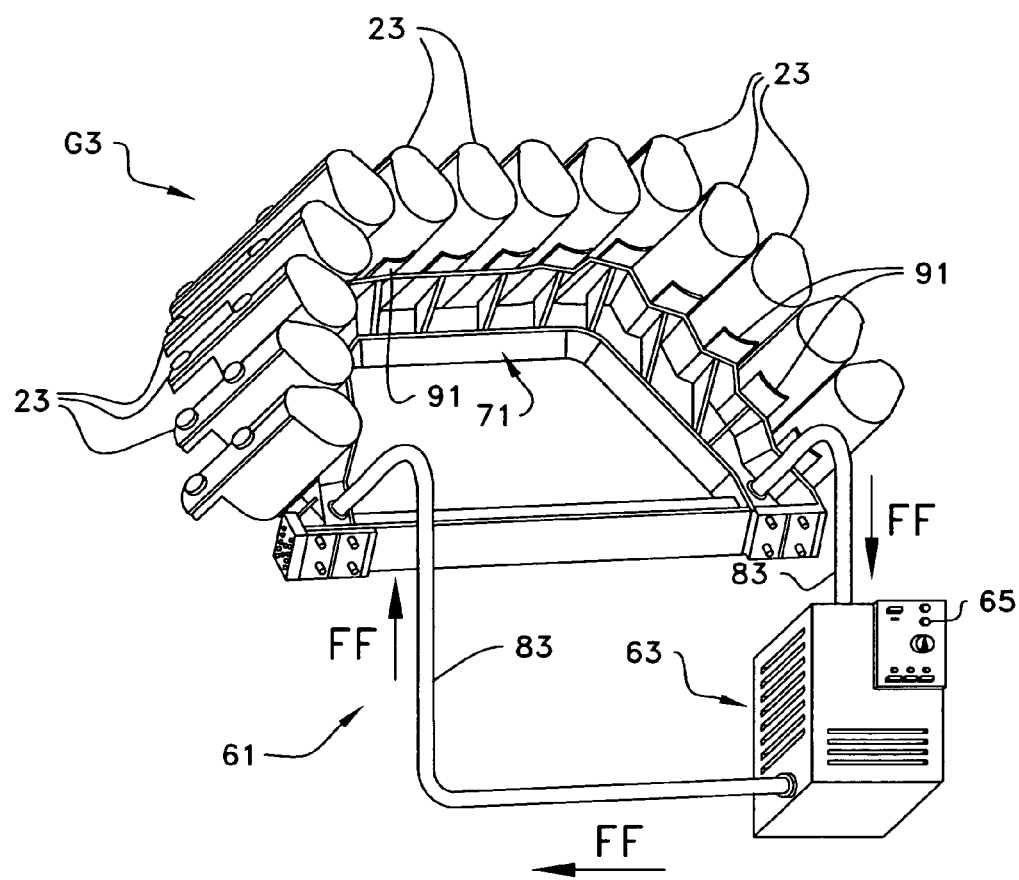
FIG. 6 is an enlarged, partial view showing one bank of imaging devices used in the apparatus shown in FIGS. 1 and 2, and one embodiment of a cooling structure designed for cooling all of the imaging devices which form part of this bank of devices.

As seen in FIGS. 1 and 2, inspection devices 23 are arranged in three groupings G1, G2 and G3, with each grouping oriented in a particular orientation relative to the conveyor and thereby to the path of travel of the articles through the apparatus. Each grouping directs X-ray beams along a plane onto the articles, there thus being a total of three planes of beams (A, B and C, shown in FIGS. 3 and 4) each article passes through while being inspected. In one embodiment, groupings G1 and G2 each include seven devices 23, and direct beams from opposite sides of the apparatus in a substantially horizontal manner, such that each article passing through the apparatus will receive beams toward the sides thereof. Grouping G3, as also seen in FIG. 6, includes fourteen devices 23 and directs beams from the top of the apparatus downwardly onto the articles, so that said articles will receive beams on the tops thereof. Each article is thus subject to pluralities of beams on at least three sides thereof. As the articles move through the three scan planes A, B and C, a number of lines of projection image data are formed for the scanned article in each scan plane. These lines of projection image data show the attenuation of the X-rays by the article and the object(s) (if any) therein. The density of an object scanned within the package can be calculated from the attenuation of the X-rays caused by the object.

When multiple X-ray devices 23 such as shown are used and arranged in groupings each oriented in a substantially planar array, as also shown, devices located near the center of a side of the image area will provide a higher intensity beam on a detector array (located opposite the devices for each grouping, one grouping of such detectors being represented by the numeral 27 in FIG. 1) because intensity decreases with the square of d, the distance of the device (source) from the detector element. Since the output of the detector elements of the detector array for all source locations should be equal, in the absence of an article such as a suitcase 25, it is necessary to progressively reduce the current for source locations as these approach the center of a side of the image for straight line source arrays. The same effect of maximizing the dynamic range of the system by substantially equalizing the output of the detectors in the detector array can also be achieved by curving the source array to progressively increase the distance between the sources and the detector arrays as the sources approach the center of the image area. This configuration provides substantially better coverage of the image area. Detectors used in each grouping 27 (three total, to accommodate the three groups of devices 23) and capable of performing in the manner defined herein are preferably of conventional construction and thus known in the art. Further description of this operation is provided in the above-mentioned U.S. Pat. No. 6,236,709.

To adapt the system for multi-spectral XCT reconstruction, each detector array 27 outputs five energy levels for each scan to provide multiple energies for the same set of data points. As mentioned or understood from the foregoing patents, systems of this type which use multiple filters to obtain multi-energy outputs from a detector are known. Alternatively, the detector systems can be constructed so that each detector provides an output signal to five comparators, each of which receives a different threshold voltage from a threshold source. The output of each comparator is a different energy level signal which represents the intensity of the spectral range above the comparator threshold input. The proportional decrease in the number of photons is a function of material chemical composition (i.e. atomic number).

The processing and analysis assembly 28 (FIG. 1) for the imaging apparatus of the invention is preferably similar to that used in U.S. Pat. No. 6,236,709, is mentioned above. This assembly receives inputs from a sensor unit which includes the detector arrays 27. A preprocessing unit interfaces directly with the sensor units to provide buffering of the output data received from the sensor units. Timing is controlled by an input from a shaft encoder. Once the five level input has been received and stored by the preprocessing unit from each of the detector arrays for a single scan, an address generator in the preprocessing unit which is connected to a plurality of reconstruction signal processing boards generates a board address to determine which of the reconstruction signal processing boards will receive a current frame of data. Each reconstruction board, as defined in U.S. Pat. No. 6,236,709, contains several (e.g., up to sixteen) computer chips. These systems cooperate to provide calibration and normalization of the raw input data, and then conventional multi-spectral XCT reconstruction which includes algebraic reconstruction. During this reconstruction, each slice through the article being inspected is reconstructed at five different energies which are required to obtain the atomic number of an inspected (sensed) object.

The algebraic reconstruction data is then sent to a detection and segmentation section of the apparatus which detects the atomic number and density of a scanned object located within one of the articles. For most materials, the linear X-ray attenuation coefficient mu is proportioned to the density. Thus the logarithm of the relative intensity of the X-ray beam is proportioned to the integral of the density of the material within the beam. The density and atomic number information is compared in a classification unit with information (criteria) within a reference table containing density and atomic number information for specific objects to be identified. This identification data and the reconstructed image data is then sent (preferably over a VME bus to a VME computer). The reconstructed XCT image data is displayed on the operator's console for review by the apparatus operator (and others, if desired). Processing of the data obtained from the scanning is preferably accomplished using the methodology (including the described ART algorithm, which employs a square grid of basis functions, centered at defined pixel locations all of the same form and diameter) described in U.S. Pat. No. 6,236,709, and further description is not believe necessary.

Figure 3:
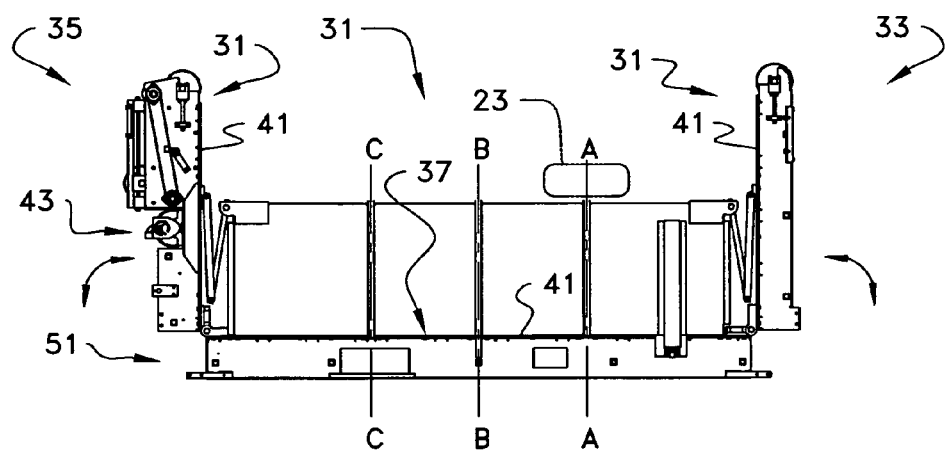
FIGS. 3 and 4 are side, elevational views, illustrating one embodiment of the invention in which a conveyor is used, the conveyor adapted for assuming both raised (closed) and lowered (opened, operating) positions, respectively, FIG. 4 being smaller in scale.
Figure 4:
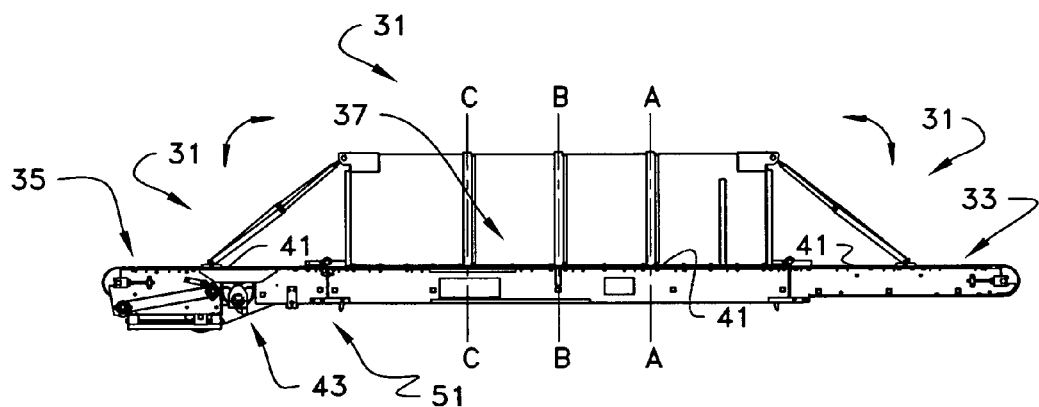

FIGS. 3-5 better illustrate a conveyor 31, which is used in this embodiment of the invention. Conveyor 31 includes three portions, a main body portion 37, and two opposing end portions 33 and 35. End portion 33 is also seen in FIG. 1, while opposite end portion 35 is also seen in FIG. 2, both of these end portions 33 and 35 in FIGS. 1 and 2 being in the withdrawn, closed position. As such, these ends are substantially vertically oriented relative to the main body portion 37 of conveyor 31. Also seen in FIGS. 3 and 4 are the three planes A, B and C, along which the groupings G1, G2 and G3 of devices 23 project their respective beams. Devices 23 are not shown in FIGS. 3 and 4 for ease of illustration, but it is understood from the above and FIGS. 1 and 2 that these devices would be positioned in a substantially planar grouping such that the planes A, B and C pass through substantially the center of a respective one of said groupings. One such device 23 is shown in phantom in FIG. 3 to illustrate this positioning orientation. Others are shown partly in FIG. 5, these devices forming part of groupings G1 and G2. The overhead devices of Grouping G3 are not shown in FIG. 5, but are clearly shown in the partial view of FIG. 6, including as mounted on the apparatus frame structure 53 (described in greater detail below).

Conveyor 31 is shown in FIG. 4 as being in its substantially flat (or planar) operating position to accept and pass (move) articles such as suitcase 25 there-along. In one embodiment, articles are placed on portion 33 and conveyed (moved) to the body portion 37 and finally to the remaining end portion 35, from which it is then removed (or drops off) the conveyor. During such movement, the article passes through planes A, B and C, where individual groupings of scans are taken. As defined in the above-identified co-pending patent application assigned to the same Assignee as the instant invention, this movement occurs with substantially no adverse motion (e.g., excessive vibration) using the conveyor of this invention, such adverse motion, as explained above, possibly altering the readings of the scanned article. The apparatus of the co-pending application accomplishes this unique motion using a single belt 41 and a single drive (motor) 43, while spacedly positioning the conveyor having these two components thereon upon a support deck structure 51 (see especially FIG. 5) separate from the frame structure 53 that holds the remainder of the apparatus, including particularly devices 23 and the detectors of each grouping 27. This spacing is best seen in FIG. 5. There is thus no need to synchronize multiple belts, thereby also reducing the complexity of the invention over many prior such apparatus. Of further notation, drive motor 43 is located on end portion 35, even further spacing it from the main support structure for the apparatus remainder. In this arrangement, articles are conveyed along at a constant speed, the belt sliding over the spacedly positioned and rigid (in a preferred embodiment, the support deck structure is made of steel) support deck structure 51 which assure accurate planarity of the belt during such movement. The above capability is made possible while also providing a conveyor structure which can be significantly reduced in length by folding of the two end portions to the closed, non-operating position, to facilitate shipping and other handling, as well as servicing and inspection, of apparatus 21. Understandably, these capabilities represent significantly advantageous features over complex apparatus such as described in the above co-pending patent application.

In one embodiment, the drive motor 43 is a one horsepower, 480 VAC, three phase, reversible electric motor with rubber lagging for enhanced belt traction. The rollers used to carry the belt are each of about 6.5 inch diameter and crowned for belt tracking. The belt itself possesses a width of one meter (39.3 inches). The belt speed may vary from about 1.22 to about 36.6 meters per minute (or about four to 120 feet per minute). The motor speed is controlled using a variable frequency drive.

In FIG. 6, there is shown one embodiment of a cooling structure 61 for directing cooling fluid substantially through the frame structure of apparatus 21 relative to the heat-generating imaging devices 23, to cool these devices during operation thereof and thereby extend the lives of said devices and cool the ambient about the apparatus. Structure 61 includes a heat exchanger 63 for cooling the desired fluid as it moves there-through. In a preferred embodiment, exchanger 63 includes an internal pump (not shown) for also pumping the fluid through the apparatus in the manner defined herein. If such a pump is not available as part of such an exchanger, a separate one will be utilized. As is understood, the cooling fluid is heated by imaging devices 23 and is thereafter effectively cooled and re-routed through the passage system taught herein to maintain the devices at effective operating temperatures much cooler than if not so cooled. A suitable heat exchanger is one sold under the product designation "M 150" from the Thermo Electron Corporation, having a business address at 25 Nimble Hill Road, Newington, N.H. This exchanger has a cooling capacity at 20 degrees Celsius of greater than 17,000 BTU (British Thermal Units), and operates at 6045 watts. It is of compact design, uses a positive displacement pump and is UL (Underwriters Laboratory) compliant. A preferred coolant is also sold by Thermo Electron Corporation under the product designation "R404A" and is classified by this company as a CFC-free refrigerant. Standard controls 65 are used to program and otherwise control the coolant temperature. This coolant is, understandably, a liquid and other liquids, including water (e.g., de-ionized water), may be utilized. It is also within the scope of the invention to utilize selected gases, including air, but the preferred medium is a liquid coolant. Structure 61 incorporates as part thereof a portion 71 of the frame structure 53 designed for holding devices 23 (here, group 3, including the mentioned fourteen devices) thereon. Portion 71 is also partly seen in FIG. 2. In a preferred embodiment, portion 71 (as well as all of the part of frame structure 53 designed for having imaging devices 23 secured thereto in a direct physical relationship) is of sound heat conducting material (a preferred example being aluminum) and, significantly, includes a plurality of passages 81 (FIG. 7) therein. In one example, two passages 81 are used, with the cooling fluid passing in the same direction (FF) in both. Fluid flow direction FF is also shown in FIG. 6, as it passes through piping 83 coupled at opposing ends of portion 71 and to exchanger 63. Piping 83 is also preferably aluminum, and is coupled to the various elements shown using conventional means.

It is understood there are three cooling structures for use with the apparatus of FIG. 1, one for each of the groupings of imaging devices 23. The structure in FIG. 6 is representative of one of these, with the other two each incorporating a portion of frame structure 53 and including passages therein for fluid flow, in addition to suitable piping. (These other two are now shown herein as it is readily understood from the illustration provided in FIG. 6 as to the make-up thereof.) In one example, it may be possible to couple each of the three frame portions to exchanger 63 rather than require use of three exchangers, provided the exchanger is capable of effectively cooling the devices 23 of all three groupings.

Figure 7:
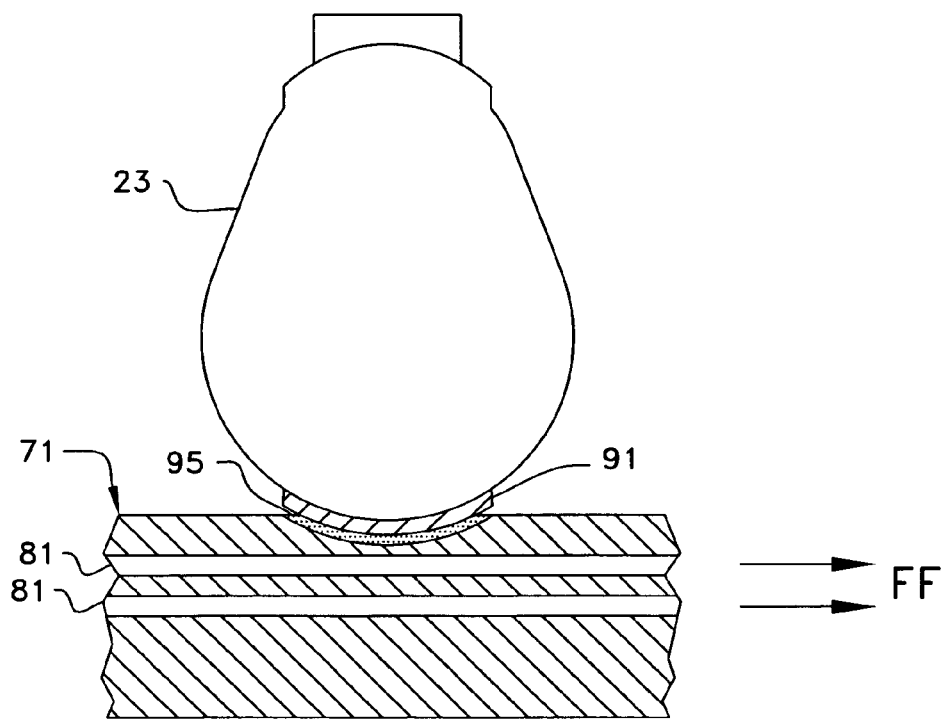
FIG. 7 is a much enlarged, partial view, partly in section, showing a part of the frame of the invention's apparatus and the cooling passages therein according to one embodiment of the invention. One example of a thermally conducting medium designed to enhance coupling between the frame and one of the invention's devices is also shown.

FIG. 7, of a more enlarged scale than FIG. 6, depicts just one imaging device 23 positioned on a part of portion 71 of the apparatus frame structure. As understood from the foregoing, device 23 may be from any of the three groupings G1, G2 or G3. In one embodiment, device 23 includes a supporting base member 91 (also shown in FIG. 6) which is secured (e.g., using bolts, not shown) to portion 71. Preferably, a thermal conducting medium 95 is also used for thermally coupling each of said heat-generating imaging devices 23 to portion 71, a preferred example of such a medium 95 being conventional thermal grease used in electronic applications such as between heat generating semiconductor chips and heat-sinks thermally bonded thereto. Generally speaking, there are two types of thermal greases: electrically conductive and electrically non-conductive. Non-conductive greases are known to include such materials as silicone and zinc, while conductive include such materials as silver, copper and aluminum. The latter are considered superior thermal conductors and thus preferred for use herein, albeit the others are also acceptable. One example is Antec "CPU Silver Thermal Grease", available from Antec Corporation, having an office at 47900 Freemont Blvd., Freemont, Calif. Several additional commercially available thermal greases are known in the industry and acceptable for use herein. Further description is not considered necessary.

Thus there has been shown and described a method of making an imaging inspection apparatus which assures effective cooling of the heat-generating imaging devices used therein so as to assure effective operation thereof. The cooling structures shown and defined herein are capable of effectively cooling the heat-generating imaging devices to thus enhance the operational life of each, while effectively cooling the ambient about apparatus 21.

While there have been shown and described what are at present the preferred embodiments of the invention, it will be obvious to those skilled in the art that various changes and modifications may be made therein without departing from the scope of the invention as defined by the appended claims. For example, increasing the area of physical contact between supporting base member 91 and portion 71 of frame structure 53 will in turn increase the thermal transference in this area. It is also possible to add more cooling passages 81 within portion 71, in addition to providing some with reverse flow in comparison to others, thus creating a "counter flow' effect, both of these modifications also increasing the cooling capacity of the invention. Further modifications are within the talents of one skilled in the art.

What is claimed is:

1. A method of making an imaging inspection apparatus for inspecting objects located within articles, said method comprising:
   providing a frame structure including a plurality of passages therein and an inspection location located substantially therein;
   positioning from twenty to forty XCT scanning devices on said frame structure adjacent said inspection location, said XCT scanning devices adapted for directing X-rays onto articles at said inspection location to thereby inspect said articles and for providing output signals as a result of said inspecting;
   positioning a processing and analysis assembly on said frame structure, said processing and analysis assembly adapted for receiving said output signals from said XCT scanning devices and for analyzing said output signals to identify said objects within said articles; and
   providing a cooling structure adapted for directing cooling fluid through said plurality of passages within said frame structure relative to said XCT scanning devices to cool said XCT scanning devices during operation thereof.

2. The method of claim 1 wherein said positioning of said XCT scanning devices on said frame structure comprises positioning said devices in at least three groupings such that each of said groupings of said XCT scanning devices is adapted for directing said X-rays along a different plane within said imaging inspection apparatus.

3. The method of claim 2 wherein said positioning of said XCT scanning devices on said frame structure in said at least three groupings comprises positioning a first of said at least three groupings substantially vertically above said inspection location and positioning second and third groupings of said XCT scanning devices along opposite sides of said inspection location.

4. The method of claim 3 wherein the number of said XCT scanning devices in said first grouping is fourteen and the number of said XCT scanning devices in each of said second and third groupings is seven.

5. The method of claim 1 further including positioning a plurality of X-ray detectors on said frame structure for receiving said X-rays from selected ones of said XCT scanning devices as said X-rays pass through said articles.

6. The method of claim 1 further including further providing means for directing said cooling fluid through said plurality of passages within said frame structure in a reverse flow manner to create a counter flow effect.

7. The method of claim 1 further including positioning thermal conducting medium within said apparatus which is adapted for thermally coupling each of said heat-generating imaging devices and said frame structure.

8. The method of claim 1 further including providing a pump, said pump adapted for accomplishing said directing of said cooling fluid relative to said heat-generating imaging devices to cool said devices during operation thereof.

9. The method of claim 1 further including providing a heat exchanger for cooling said cooling fluid.

10. The method of claim 1 further including providing temperature control means for controlling the temperature of said cooling fluid.

11. The method of claim 1 further including providing a conveyor for conveying said articles having said objects located therein along a path of travel through said inspection location.

12. The method of claim 11 wherein said conveyor is positioned within said apparatus so as not to be physically coupled to said frame structure and is also adapted for being folded to an orientation of a lesser length than that of said conveyor when said conveyor is conveying said articles along said path of travel.

13. The method of claim 11 wherein said conveyor is provided in the form of a single belt.

14. The method of claim 13 further including providing a single drive for driving said single belt.

15. The method of claim 13 wherein said single belt conveyor is provided with first, second and third portions such that said first portion includes a body portion and said second and third portions each include end portions located at opposite ends of said body portion, and such that each of said second and third end portions are adapted for being moved to a position substantially perpendicular to said body portion.

* * * * *